US010408750B2

(12) United States Patent
Kondo et al.

(10) Patent No.: US 10,408,750 B2
(45) Date of Patent: Sep. 10, 2019

(54) VOID-ARRANGED STRUCTURE AND MEASUREMENT METHOD USING THE SAME

(71) Applicant: Murata Manufacturing Co., Ltd., Nagaokakyo-shi, Kyoto-fu (JP)

(72) Inventors: Takashi Kondo, Nagaokakyo (JP); Seiji Kamba, Nagaokakyo (JP); Kazuhiro Takigawa, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 213 days.

(21) Appl. No.: 14/862,340

(22) Filed: Sep. 23, 2015

(65) Prior Publication Data

US 2016/0011104 A1    Jan. 14, 2016

Related U.S. Application Data

(63) Continuation of application No. PCT/JP2014/056619, filed on Mar. 13, 2014.

(30) Foreign Application Priority Data

Mar. 25, 2013 (JP) ................. 2013-062285

(51) Int. Cl.
*G01N 21/3586* (2014.01)
*G01N 21/01* (2006.01)
(Continued)

(52) U.S. Cl.
CPC ......... *G01N 21/3586* (2013.01); *G01N 21/01* (2013.01); *G01J 1/00* (2013.01);
(Continued)

(58) Field of Classification Search
CPC ....... G01N 21/3586; G01N 21/01; G01J 3/02; G01J 1/00; G01J 5/00; G01J 1/0422;
(Continued)

(56) References Cited

U.S. PATENT DOCUMENTS 5,973,316 A * 10/1999 Ebbesen ................ B82Y 20/00
250/216
6,236,033 B1 * 5/2001 Ebbesen ................ B82Y 20/00
250/216
(Continued)

FOREIGN PATENT DOCUMENTS

JP    2004-288240 A    10/2004
JP    2007-163181 A    6/2007
(Continued)

OTHER PUBLICATIONS

International Search Report issued for PCT/JP2014/056619, dated Jun. 10, 2014.
(Continued)

*Primary Examiner* — David P Porta
*Assistant Examiner* — Djura Malevic
(74) *Attorney, Agent, or Firm* — Arent Fox LLP

(57) ABSTRACT

A void-arranged structure that includes a pair of principal surfaces opposing each other and a plurality of void sections that penetrate through the pair of principal surfaces. The void-arranged structure is configured of a plurality of unit structures each of which includes a first void section and a second void section having a different shape from a shape of the first void section, and the overall shape of the unit structure, when the principal surface is viewed from above, is not mirror-symmetric with respect to a predetermined imaginary plane orthogonal to the principal surface of the void-arranged structure.

5 Claims, 12 Drawing Sheets

(51) Int. Cl.
- *G01J 1/04* (2006.01)
- *G01J 3/02* (2006.01)
- *G01J 3/12* (2006.01)
- *G01J 1/00* (2006.01)
- *G01J 5/08* (2006.01)
- *G01J 5/00* (2006.01)

(52) U.S. Cl.
CPC ........... *G01J 1/0422* (2013.01); *G01J 1/0437* (2013.01); *G01J 3/02* (2013.01); *G01J 3/0216* (2013.01); *G01J 3/0229* (2013.01); *G01J 3/0243* (2013.01); *G01J 5/00* (2013.01); *G01J 5/0831* (2013.01); *G01J 2001/0481* (2013.01); *G01J 2003/1278* (2013.01); *G01N 2201/02* (2013.01); *G01N 2201/068* (2013.01); *G01N 2201/0697* (2013.01); *G01N 2201/06113* (2013.01); *G01N 2201/12* (2013.01)

(58) Field of Classification Search
CPC ............. G01J 1/0437; G01J 2001/0481; G01J 3/0216; G01J 3/0243; G01J 3/0229; G01J 3/05; G01J 3/0831; G01J 2003/1278
See application file for complete search history.

(56) References Cited

U.S. PATENT DOCUMENTS

| | | | | |
|---|---|---|---|---|
| 6,264,331 | B1* | 7/2001 | Sawai | G03B 21/006 353/31 |
| 6,285,020 | B1* | 9/2001 | Kim | B82Y 20/00 250/201.3 |
| 7,242,478 | B1* | 7/2007 | Dombrowski | G01J 3/02 356/419 |
| 8,304,732 | B2* | 11/2012 | Kamba | G01N 21/3581 250/341.3 |
| 8,535,616 | B2* | 9/2013 | Blair | B82Y 20/00 250/201.3 |
| 8,847,345 | B2* | 9/2014 | Handa | B82Y 20/00 250/208.1 |
| 9,117,762 | B2* | 8/2015 | Shin | H01L 21/308 |
| 2003/0148401 | A1* | 8/2003 | Agrawal | B01J 19/0046 506/9 |
| 2003/0173501 | A1* | 9/2003 | Thio | B82Y 20/00 250/216 |
| 2004/0110092 | A1* | 6/2004 | Lin | G03F 7/001 430/311 |
| 2007/0015088 | A1* | 1/2007 | Lin | G03F 1/36 430/311 |
| 2007/0125956 | A1* | 6/2007 | Buschbeck | B82Y 10/00 250/396 R |
| 2010/0025586 | A1* | 2/2010 | Ogawa | G01N 21/3581 250/341.1 |
| 2010/0271692 | A1 | 10/2010 | Hor et al. | |
| 2011/0017910 | A1* | 1/2011 | Nagel | G01N 21/3581 250/338.4 |
| 2011/0124194 | A1* | 5/2011 | Kwon | H01L 21/0337 438/692 |
| 2011/0211105 | A1* | 9/2011 | Yamada | B29D 11/00298 348/340 |
| 2011/0222056 | A1* | 9/2011 | Seo | G01J 3/02 356/303 |
| 2011/0299104 | A1* | 12/2011 | Seo | G01J 3/02 358/1.9 |
| 2012/0032082 | A1* | 2/2012 | Pradere | G01N 21/3581 250/341.1 |
| 2012/0153159 | A1* | 6/2012 | Kamba | G01N 21/3581 250/341.3 |
| 2012/0235043 | A1* | 9/2012 | Ogawa | G01N 21/3581 250/341.1 |
| 2013/0182251 | A1* | 7/2013 | Shimbo | G01J 3/0208 356/302 |
| 2013/0189592 | A1* | 7/2013 | Roumi | H01G 9/048 429/406 |
| 2013/0221209 | A1* | 8/2013 | Kamba | G01N 21/3581 250/225 |
| 2014/0030894 | A1* | 1/2014 | Shin | H01L 21/308 438/703 |
| 2014/0091409 | A1* | 4/2014 | Murarka | B81C 1/00634 257/419 |
| 2014/0252235 | A1* | 9/2014 | Kondo | G01N 21/253 250/341.1 |
| 2015/0136989 | A1* | 5/2015 | Kondo | G01N 21/3586 250/341.1 |
| 2016/0011104 | A1* | 1/2016 | Kondo | G01N 21/3586 250/339.07 |
| 2017/0017018 | A1* | 1/2017 | Chao | G02B 3/0018 |

FOREIGN PATENT DOCUMENTS

| | | |
|---|---|---|
| JP | 2008-185552 A | 8/2008 |
| JP | 2011-515688 A | 5/2011 |
| WO | WO 2011/027642 A1 | 3/2011 |
| WO | WO 2012/029629 A1 | 3/2012 |
| WO | WO 2013/035371 A1 | 3/2015 |

OTHER PUBLICATIONS

Lee et al.; "Shape resonance omni-directional terahertz filters with near-unity transmittance"; Optics Express, Feb. 6, 2006, vol. 14, No. 3, pp. 1253-1259.

Singh et al.; "Random terahertz metamaterials"; Journal of Optics. 2010, vol. 12, No. 1, pp. 1-5.

Written Opinion of the International Searching Authority issued for PCT/JP2014/056619, dated Jun. 10, 2014.

\* cited by examiner

VOID-ARRANGED STRUCTURE AND MEASUREMENT METHOD USING THE SAME

CROSS REFERENCE TO RELATED APPLICATIONS

The present application is a continuation of International application No. PCT/JP2014/056619, filed Mar. 13, 2014, which claims priority to Japanese Patent Application No. 2013-062285, filed Mar. 25, 2013, the entire contents of each of which are incorporated herein by reference.

FIELD OF THE INVENTION

The present invention relates to a void-arranged structure used for measuring presence/absence or quantity of a measurement object by irradiating the void-arranged structure holding the measurement object with electromagnetic waves and detecting characteristics of the electromagnetic waves scattered at the void-arranged structure, and also relates to a measurement method using the stated void-arranged structure.

BACKGROUND OF THE INVENTION

In order to analyze characteristics of substances, a measurement method in which a measurement object is held by a void-arranged structure (a structure having a plurality of voids), the void-arranged structure holding the measurement object is irradiated with electromagnetic waves, and then a transmission spectrum thereof is analyzed to detect the characteristics of the measurement object has been conventionally used. To be more specific, a method in which a measurement object, such as a protein, that is attached to a metal mesh filter is irradiated with terahertz waves so as to analyze the transmission spectrum can be cited, for example.

As a conventional technique of the transmission spectrum analysis method using electromagnetic waves as described above, for example, Patent Document 1 (Japanese Unexamined Patent Application Publication No. 2008-185552) discloses a measurement method in which electromagnetic waves are emitted to strike a void-arranged structure having a void region (specifically, a mesh-formed conductor plate), where a measurement object is held, in an oblique direction with respect to a principal surface of the void-arranged structure, and the electromagnetic waves that have passed through the void-arrange structure are measured so as to detect characteristics of the measurement object based on a phenomenon that the position of a dip waveform generated in the measured frequency characteristic moves depending on presence/absence of the measurement object.

In addition, Patent Document 2 (International Publication No. WO 2011/027642) discloses a measurement method in which a void-arranged structure having a void whose shape is not mirror-symmetric with respect to an imaginary plane orthogonal to a polarizing direction of electromagnetic waves is used, and the void-arranged structure is irradiated with the electromagnetic waves in a direction perpendicular to a principal surface of the void-arranged structure so as to measure characteristics of the measurement object using the frequency characteristic of the electromagnetic waves having been scattered. In this method, because the electromagnetic waves strike the void-arranged structure in the direction perpendicular to the principal surface of the void-arranged structure, measurement errors due to a variation in incident angle of the electromagnetic waves can be suppressed in comparison with the case where the electromagnetic waves strike the void-arranged structure in the oblique direction. Accordingly, this method has an advantage that measurement sensitivity can be improved.

However, a measurement method that exhibits a higher sensitivity and a higher reproducibility than the above-described methods has been required to be provided.

Patent Document 1: Japanese Unexamined Patent Application Publication No. 2008-185552
Patent Document 2: International Publication No. WO 2011/027642

SUMMARY OF THE INVENTION

An object of the present invention is to provide a void-arranged structure capable of measuring presence/absence or quantity of a measurement object at a high level of measurement sensitivity and reproducibility.

An aspect of the present invention is a void-arranged structure that is used for measuring presence/absence or quantity of a measurement object by irradiating the void-arranged structure on which the measurement object is held with electromagnetic waves and detecting characteristics of the electromagnetic waves having been scattered at the void-arranged structure.

The void-arranged structure includes a pair of principal surfaces opposing each other and a plurality of void sections that are so formed as to penetrate through the pair of principal surfaces.

The void-arranged structure is configured of a plurality of unit structures each of which has the same shape and includes at least two above-mentioned void sections aligned at a predetermined interval, and which are connected two-dimensionally and periodically along a direction of the principal surface.

The unit structure includes a first void section and a second void section having a different shape from that of the first void section.

The overall shape of the unit structure, when the principal surface is viewed from above, is not mirror-symmetric with respect to a predetermined imaginary plane orthogonal to the principal surface of the void-arranged structure.

It is preferable for the imaginary plane to be a plane perpendicular to a polarizing direction of the electromagnetic waves. In addition, it is preferable for a shape of the first void section not to be mirror-symmetric with respect to the imaginary plane.

It is preferable for a ratio of the number of the first void sections to the total of the void sections included in the above unit structure to be greater than 50%.

It is more preferable for the ratio of the number of the first void sections to the total of the void sections included in the above unit structure to be equal to or greater than 75%.

An aspect of the present invention relates to a measurement method for measuring a measurement object, the method includes:

holding the measurement object on the void-arranged structure;

irradiating the void-arranged structure on which the measurement object is held with electromagnetic waves and detecting characteristics of the electromagnetic waves having been scattered at the void-arranged structure; and calculating presence/absence or quantity of the measurement object using the detected characteristics of the electromagnetic waves.

It is preferable for the electromagnetic waves to strike the void-arranged structure in a direction perpendicular to a principal surface of the void-arranged structure.

According to the void-arranged structure of the present invention, each unit structure configuring the void-arranged structure includes the first void section and the second void section having a different shape from that of the first void section, and the overall shape of the unit structure, when the principal surface of the void-arranged structure is viewed from above, is not mirror-symmetric with respect to a predetermined imaginary plane orthogonal to the principal surface of the void-arranged structure, whereby a ratio of a portion in a surface of the void-arranged structure where a current density is small when the void-arranged structure is irradiated with electromagnetic waves, can be decreased, and in particular, a current density in an inner wall of the void section can be increased. This makes it possible to increase a change in characteristics of the scattered electromagnetic waves when the measurement object is attached to the void-arranged structure and improve the measurement sensitivity.

Further, in the case where the imaginary plane is a plane perpendicular to a polarizing direction of the electromagnetic waves and the first void section has a shape being not mirror-symmetric with respect to the imaginary plane, the electromagnetic waves can strike the void-arranged structure in a direction perpendicular to the principal surface thereof, whereby measurement errors due to a variation in incident angle of the electromagnetic waves can be reduced or eliminated in comparison with the case where the electromagnetic waves are incident on the void-arranged structure in an oblique direction so that the measurement sensitivity in measuring the measurement object is improved.

BRIEF DESCRIPTION OF THE DRAWINGS

FIG. 15(a) being a perspective view and FIG. 15(b) being a front view.

DETAILED DESCRIPTION OF THE PREFERRED EMBODIMENTS

Figure 14:
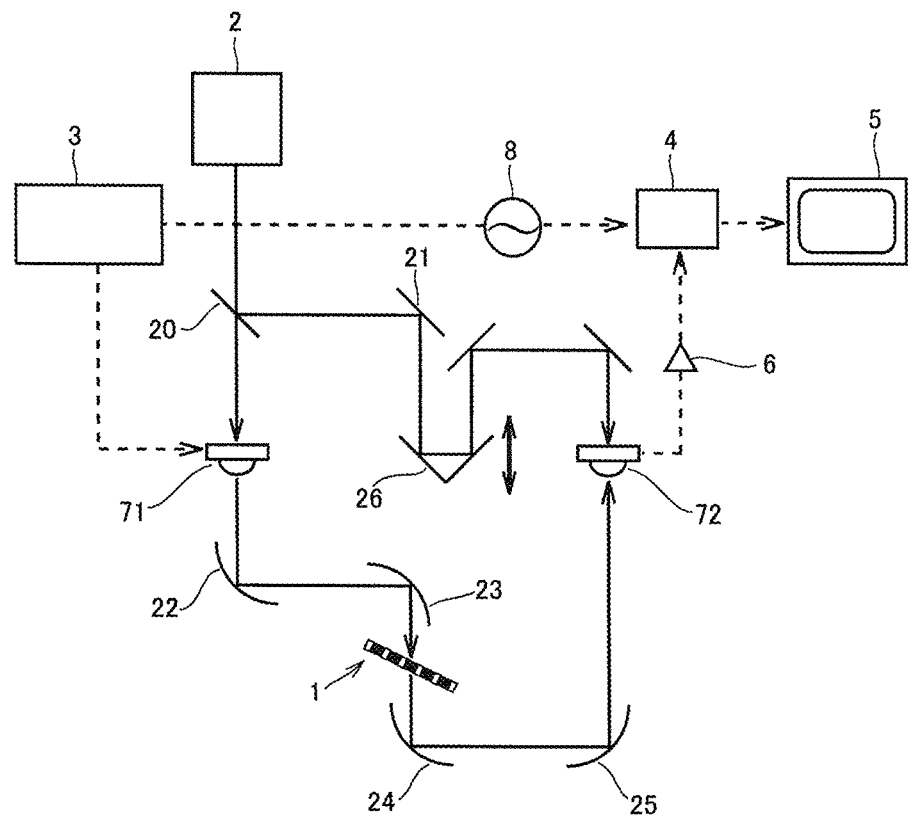
FIG. 14 is a schematic diagram for explaining an example of a measurement method using a void-arranged structure according to the present invention.

First, an example of a measurement method using a void-arranged structure of the present invention will be described with reference to FIG. 14. FIG. 14 is a diagram schematically illustrating the overall structure of a measurement apparatus for measurement operation. This apparatus uses electromagnetic wave pulses (for example, terahertz wave pulses at a frequency of 20 GHz to 120 THz) generated by irradiating a semiconductor material with a laser beam emitted from a laser 2 (for example, a short optical pulse laser).

In the configuration shown in FIG. 14, a laser beam emitted from the laser 2 branches to two paths at a half mirror 20. One of them strikes a photoconductive element 71 on the electromagnetic wave generation side, and the other one is allowed to pass a time delay stage 26 and strike a photoconductive element 72 on the reception side by using a plurality of mirrors 21 (attachment of reference numerals to the mirrors having the same function is omitted). As the photoconductive elements 71 and 72, a typical element such that a dipole antenna having a gap section is formed on LT-GaAs (low temperature growth GaAs) can be used. Further, as the laser 2, a fiber type laser, a laser using a solid such as titanium sapphire, or the like can be used. Furthermore, for the generation or detection of electromagnetic waves, a semiconductor surface without an antenna or electro-optical crystal such as ZnTe crystal may be used. Note that an adequate bias voltage is applied to a gap section of the photoconductive element 71 on the generation side by a power supply 3.

Generated electromagnetic waves are converted to a collimated beam by a parabolic surface mirror 22 and guided to strike a void-arranged structure 1 by a parabolic surface mirror 23. Terahertz waves having passed through the void-arranged structure 1 are guided by parabolic surface mirrors 24 and 25 to be received by the photoconductive element 72. The electromagnetic waves received by the photoconductive element 72 are amplified by an amplifier 6 and then acquired as a time waveform by a lock-in amplifier 4. Subsequently, signal processing such as Fourier transformation or the like is performed on the acquired waveform in a PC (personal computer) 5 including a calculation means, thereafter, a transmittance spectrum or the like of the void-arranged structure 1 is calculated. In order to ensure the above acquisition by the lock-in amplifier 4, a bias voltage that is outputted from the power supply 3 and applied to the gap of the photoconductive element 71 on the generation side is modulated (amplitude: 5V-30V) with a signal of an oscillator 8. With this, synchronous detection is carried out, and therefore, a signal to noise ratio (S/N ratio) can be improved.

The measurement method discussed above is generally called a terahertz time domain spectroscopy (THz-TDS).

In FIG. 14, the case where scattering occurs in the mode of transmitting, that is, the case in which transmittance of the electromagnetic waves is measured is illustrated. Note that the term "scattering" in the present invention means a broad concept including transmission as one mode of forward scattering, reflection as one mode of backward scattering, and the like. Here, it is preferable to be transmission or reflection, and more preferable to be transmission in a zero-order direction, reflection in a zero-order direction, and the like.

In general, in the case where a lattice interval of a diffraction grating (corresponds to an interval of a void section in the present specification) is taken as "d", an incident angle is taken as "i", a diffraction angle is taken as θ, and a wave length is taken as λ, a spectrum diffracted by the diffraction grating can be represented as follows.

$$d(\sin i - \sin \theta) = n\lambda \quad (1)$$

Here, "zero-order" in the expression "zero-order direction" indicates a case in which n is 0 in the above formula (1). Because neither d nor λ can be 0, n=0 holds only when (sin i−sin θ) equals 0. Accordingly, the expression "zero-order direction" corresponds to a state in which the incident angle is equal to the diffraction angle, in other words, means a direction along which the electromagnetic waves travel without changing the travelling direction thereof.

Electromagnetic waves used in the measurement method discussed above are not limited to any specific ones as long as the electromagnetic waves can be scattered in accordance with a structure of the void-arranged structure, and any of radio waves, infrared rays, visible rays, ultraviolet rays, X-rays, gamma rays, and the like can be used. Further, although the frequency thereof is not limited to any specific one, electromagnetic waves at a frequency of 1 GHz to 1 PHz are preferably used, and more preferably used are terahertz waves at a frequency of 20 GHz to 120 THz. The electromagnetic waves used in the present invention are linearly polarized electromagnetic waves in general. As specific electromagnetic waves, for example, terahertz waves that are generated by the optical rectification effect of electro-optical crystal such as ZnTe or the like using a short optical pulse laser as a light source, infrared rays radiated from a high pressure mercury lamp, a ceramic lamp, or the like, visible light emitted from a semiconductor laser, electromagnetic waves radiated from a photoconductive antenna, and so on can be cited.

It is preferable that electromagnetic waves emitted to strike the void-arranged structure of the present invention be plane waves. More specifically, it is preferable that electromagnetic waves emitted from a light source strike the void-arranged structure after having been converted to plane waves (collimated light) with parabolic surface mirrors, lenses, and so on.

It is preferable that electromagnetic waves have substantially the same phase in the principal surface of the void-arranged structure at least within a range irradiated with the electromagnetic waves. In other words, it is preferable that the electromagnetic waves have substantially the same phase at every location (point) in an area, irradiated with the electromagnetic waves, of the principal surface of the void-arranged structure. The reason for this is as follows: that is, in the case of the phases being the same, a dip waveform in the transmittance spectrum (or a peak waveform in the reflectance spectrum) becomes sharper so that characteristics of the measurement object can be measured at a high level of sensitivity.

Further, it is preferable that electromagnetic waves have substantially the same amplitude in the principal surface of the void-arranged structure at least within a range irradiated with the electromagnetic waves. The reason for this is as follows: that is, in the case of the amplitudes being the same, a dip waveform in the transmittance spectrum (or a peak waveform in the reflectance spectrum) becomes sharper so that characteristics of the measurement object can be measured at a high level of sensitivity.

In the case of using the void-arranged structure of the present invention, the electromagnetic waves can strike the void-arranged structure in a direction perpendicular to the principal surface of the void-arranged structure. In this case, measurement errors due to a variation in incident angle of the electromagnetic waves can be reduced or eliminated, thereby improving the measurement sensitivity.

Note that in the present invention, to measure the presence/absence or quantity of a measurement object is to detect the presence/absence of or determine the quantity of a compound as a measurement object, and a case such that a minute quantity of a measurement object contained in a solution or the like is measured can be cited as an example. More specifically, for example, a method can be cited as follows: that is, a void-arranged structure is immersed in a solution in which a measurement object is dissolved, the measurement object is attached to a surface of the void-arranged structure, thereafter the solvent, the extra measurement object, and so on are washed out and the void-arranged structure is dried, and then the presence/absence or quantity of the measurement object is measured using the above-mentioned measurement apparatus.

(Void-Arranged Structure)

The void-arranged structure of the present invention includes a pair of principal surfaces opposing each other and a plurality of void sections formed so as to penetrate through the pair of principal surfaces. The void-arranged structure is a structure in which a plurality of unit structures each of which has the same shape and includes at least two void sections aligned at a predetermined interval are connected two-dimensionally and periodically along a principal surface direction of the void-arranged structure.

Here, the expression of void sections being "aligned at a predetermined interval" in the unit structure means that all the void sections may be periodically arranged at a predetermined interval, or some of the void sections may be arranged periodically and the rest of the void sections may be arranged non-periodically without reducing the advantageous effects of the invention. Further, the expression "a plurality of unit structures each of which has the same shape are connected two-dimensionally and periodically along a principal surface direction of the void-arranged structure" means that, for example, one principal surface of each of the unit structures is coupled with one another so as to form one principal surface of the void-arranged structure. For example, a void-arranged structure in which unit structures are periodically arranged along the principal surface of the void-arranged structure in the form of a square lattice, a triangular lattice, or the like can be cited.

Further, in the void-arranged structure of the present invention, the unit structure includes a first void section and a second void section having a different shape from that of the first void section, and the overall shape of the unit structure, when the principal surface of the void-arranged structure is viewed from above, is not mirror-symmetric with respect to a predetermined imaginary plane orthogonal to the principal surface of the void-arranged structure.

It is preferable for the void-arranged structure to be a quasi-periodic structure, a periodic structure, or the like. The quasi-periodic structure implies a structure in which translational symmetry is not held but array orderliness is maintained. Examples of the quasi-periodic structure include a Fibonacci structure as a one-dimensional quasi-periodic structure and a Penrose structure as a two-dimensional quasi-periodic structure. The periodic structure implies a structure having such spatial symmetry that is represented by translational symmetry, and is classified into one-dimensional, two-dimensional, and three-dimensional periodic structures depending on the dimension of the symmetry. Examples of the one-dimensional periodic structure include, for example, a wire grid structure, a one-dimensional grating, and the like. Examples of the two-dimensional periodic structure include, for example, a mesh filter, a two-dimensional grating, and the like. Of these periodic structures, the two-dimensional periodic structure is preferably used. Specifically, a structure that includes void sections orderly arranged at least in one array direction, or the like can be cited.

Figure 15A:
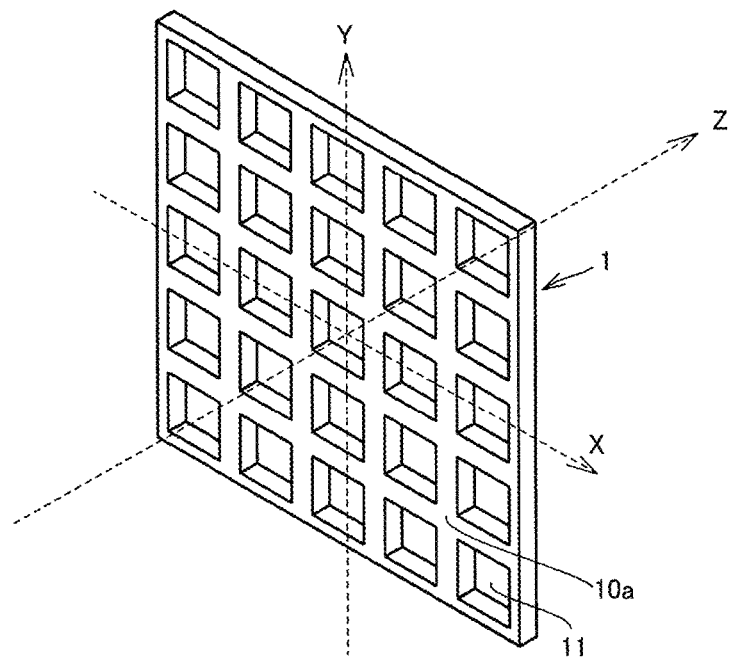
FIGS. 15(a) and 15(b) include schematic diagrams for explaining the overall configuration of a void-arranged structure.
Figure 15B:
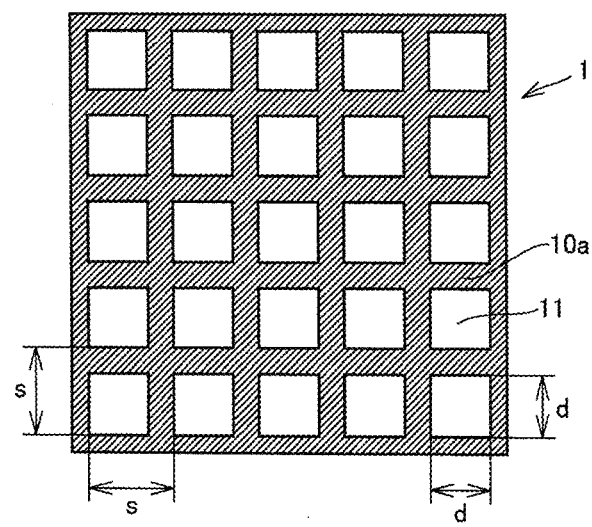

As a two-dimensional periodic structure, for example, a flat-plate structure (lattice structure) in which void sections are arranged at a constant interval in matrix form, as shown in FIGS. 15(a) and 15(b), can be cited. The void-arranged structure 1 shown in FIGS. 15(a) and 15(b) is a structure in which square void sections 11 are provided at equal intervals in the vertical and horizontal directions in the drawings when viewed from a principal surface 10a side of the structure. It is to be noted that FIGS. 15(a) and 15(b) are diagrams only for explaining the two-dimensional periodic structure (the overall configuration of the void-arranged structure) and details of the shape of the void section (a projection provided in the void section and the like) are omitted.

(Unit Structure)

In the present invention, the term "unit structure" refers to a minimum configuration unit for configuring a void-arranged structure in a periodic manner, and the unit structure is a structure including at least two void sections.

In the present invention, as described above, (i) a unit structure includes a first void section and a second void section having a different shape from that of the first void section, and (ii) the overall shape of the unit structure is not mirror-symmetric, when a principal surface of the void-arranged structure is viewed from above, with respect to a predetermined imaginary plane orthogonal to the principal surface of the void-arranged structure. Here, the term "the overall shape" of the unit structure is a shape defined by an opening shape of the void section and its arrangement.

The condition of (i) implies that the unit structure includes a plurality of first void sections and at least one second void section having a different shape from that of the first void sections, and that a case where all the void sections of the unit structure have the same shape (face the same direction) is eliminated. Here, a "different shape" includes another shape that is arranged facing a different direction. Further, the void sections included in the unit structure are not limited to the above two types (first void section, second void section).

Further, in the above-mentioned (i) and (ii), the predetermined imaginary plane orthogonal to the principal surface of the void-arranged structure is also a plane perpendicular to a polarizing direction of electromagnetic waves when the electromagnetic waves are emitted.

Although the shape of the first void section is not limited to any specific one, it is preferable for the shape thereof not to be mirror-symmetric with respect to the predetermined imaginary plane orthogonal to the principal surface of the void-arranged structure as well as perpendicular to the polarizing direction of the electromagnetic waves. In this case, measurement can be carried out even if the electromagnetic waves are emitted to strike the void-arranged structure in a direction perpendicular to the principal surface of the void-arranged structure, whereby measurement errors due to a variation in incident angle of the electromagnetic waves can be reduced or eliminated in comparison with the case where the electromagnetic waves are incident on the void-arranged structure in an oblique direction, so that the measurement sensitivity in measuring the measurement object is improved. As examples of the two-dimensional shape of the void-section which is not mirror-symmetric with respect to the imaginary plane, a trapezoid, a convex shape, a concave shape, a polygon other than regular polygons, a regular polygon with an odd number of interior angles (an equilateral triangle, an equilateral pentagon, or the like), a star-shape, and the like can be cited.

It is preferable for the number of the first void sections to be greater than 50% of the total void sections included in the unit structure, and more preferable to be equal to or greater than 75% thereof. In this case, a dip waveform or the like generated in a transmittance spectrum of the void-arranged structure tends to be sharper.

Since dimensions of the void section are appropriately designed depending on the measurement method, material characteristics of the void-arranged structure, frequencies of the electromagnetic waves to be used, and the like, it is difficult to generalize the range of the dimensions. Note that, however, in the case of detecting front-scattered electromagnetic waves, in the void-arranged structure 1 where the void sections are orderly arranged in the vertical and horizontal directions as shown in FIG. 15(a), it is preferable for a lattice interval of the void section indicated by "s" in FIG. 15(b) to be no less than one tenth of the wave length of the electromagnetic waves used in the measurement and no more than ten times the wave length thereof. In the case where the lattice interval s of the void section takes a value outside the above range, scattering is unlikely to occur in some case. Further, regarding a hole size of the void section, it is preferable for a hole size indicated by "d" in FIG. 15(b) to be no less than one tenth of the wave length of the electromagnetic waves used in the measurement and no more than ten times the wave length thereof. If the hole size of the void section takes a value outside this range, there is a case where it is difficult to detect a signal because intensity of the transmitting (front-scattering) electromagnetic waves is weakened.

Since an average thickness of the void-arranged structure is appropriately designed depending on the measurement method, material characteristics of the void-arranged structure, frequencies of the electromagnetic waves to be used, and the like, it is difficult to generalize the range of the thickness. Note that, however, in the case of detecting the front-scattered electromagnetic waves, it is preferable for the thickness to be no more than several times the wave length of the electromagnetic waves used in the measurement. If the average thickness of the structure takes a value larger than this range, there is a case where it is difficult to detect a signal because the intensity of the front-scattering electromagnetic waves is weakened.

In the present invention, as a method for holding a measurement object on the void-arranged structure, various kinds of known techniques can be used. For example, the measurement object may be directly attached to the void-arranged structure or attached to the structure with a support film or the like interposed therebetween. It is preferable to directly attach the measurement object to the surface of the void-arranged structure in view of increasing the measurement sensitivity and suppressing a variation in measurement, thereby carrying out the measurement at a high level of reproducibility.

As examples in which the measurement object is directly attached to the void-arranged structure, cited is not only a case in which chemical bonding or the like is directly formed between the surface of the void-arranged structure and the measurement object but also a case in which a host molecule is bonded to the surface of the void-arranged structure in advance and then the measurement object is bonded to the host molecule on the void-arranged structure. Examples of the chemical bonding include covalent bonding (e.g., covalent bonding between a metal and a thiol group), Van der Waals bonding, ionic bonding, metal bonding, hydrogen bonding, and the like; of these bonding examples, the covalent bonding is preferable. Note that the host molecule is a molecule or the like capable of specifically bonding the measurement object thereto; as the combination of the host molecule and the measurement object, for example, an antigen and an antibody, a sugar chain and a protein, a lipid and a protein, a low-molecule compound (ligand) and a protein, a protein and a protein, a single strand DNA and a single strand DNA, or the like can be cited.

In the case of direct attachment of a measurement object to a void-arranged structure, it is preferable to use such a void-arranged structure that at least part of the surface thereof is formed of a conductor. Here, the conductor means an object (substance) through which a current flows, and includes not only a metal but also a semiconductor. Examples of the metals include a metal capable of being bonded to a functional group of a compound having a functional group such as a hydroxyl group, a thiol group, a carboxyl group, or the like, a metal capable of coating its surface with a functional group such as a hydroxyl group, an amino group, or the kike, and an alloy of these metals. More specifically, gold, silver, copper, iron, nickel, chromium, silicon, germanium, and the like can be cited. Of these metals, gold, silver, copper, nickel, and chromium are preferable to be used, and gold and nickel are more preferable. Using gold or nickel is advantageous particularly when the measurement object contains a thiol group (—SH group) because the thiol group can be bonded to the surface of the void-arranged structure. Using nickel is advantageous particularly when the measurement object contains a hydroxyl group (—OH), a carboxyl group (—COOH), or the like because the functional group can be bonded to the surface of the void-arranged structure. Furthermore, as examples of the semiconductors, a group IV semiconductor (Si, Ge, or the like), compound semiconductors such as a group II-VI semiconductor (ZnSe, CdS, ZnO, or the like), a group III-V semiconductor (GaAs, InP, GaN, or the like), a group IV compound semiconductor (SiC, SiGe, or the like), and a group I-III-VI semiconductor (CuInSe2, or the like), as well as organic semiconductors can be cited.

Note that, for example, in the case where a surface of a portion of the void-arranged structure where a current density is relatively high (e.g., an inner wall of the void section) is covered with a substance likely to be bonded to the measurement object, the measurement object can be selectively held and a change rate of a dip waveform in the frequency characteristic of the front-scattered electromagnetic waves or a peak waveform in the frequency characteristic of the rear-scattered electromagnetic waves can be made larger by the measurement object.

It is possible to measure the characteristics of the measurement object based on at least one parameter related to the frequency characteristic of the void-arranged structure obtained in the manner discussed above. For example, the characteristics of the measurement object can be measured based on a phenomenon that a dip waveform generated in the frequency characteristic of the front-scattered (transmitted) electromagnetic waves, a peak waveform generated in the frequency characteristic of the rear-scattered (reflected) electromagnetic waves, or the like is changed by the presence of the measurement object.

Here, the dip waveform is a waveform of a valley-shaped (downward projecting) portion, which partly appears in a frequency characteristic (for example, a transmittance spectrum) of the void-arranged structure in a frequency range where a ratio of the detected electromagnetic waves to the electromagnetic waves having struck the void-arranged structure (for example, transmittance of the electromagnetic waves) is relatively large. Meanwhile, the peak waveform is a mountain-shaped (upward projecting) portion, which partly appears in the frequency characteristic of the void-arranged structure (for example, a reflectance spectrum) in a frequency range where a ratio of the detected electromagnetic waves to the electromagnetic waves having struck the void-arranged structure (for example, reflectance of the electromagnetic waves) is relatively small.

WORKING EXAMPLES

Hereinafter, the present invention will be described in detail by giving working examples. However, the invention is not limited thereto. Note that in the drawings and the like referred to in the following descriptions, the letter "Z" indicates a travelling direction of electromagnetic waves emitted for striking, the letter "Y" indicates a polarizing direction (electric field direction) of the electromagnetic waves, and the letter "X" indicates a magnetic field direction (a direction perpendicular to Y and Z). Further, in FIGS. 1, 5, 8, 10, and 12, numerical values other than the reference numerals indicate dimensions of respective portions, and a unit thereof is "mm".

Conventional Example

Figure 1:
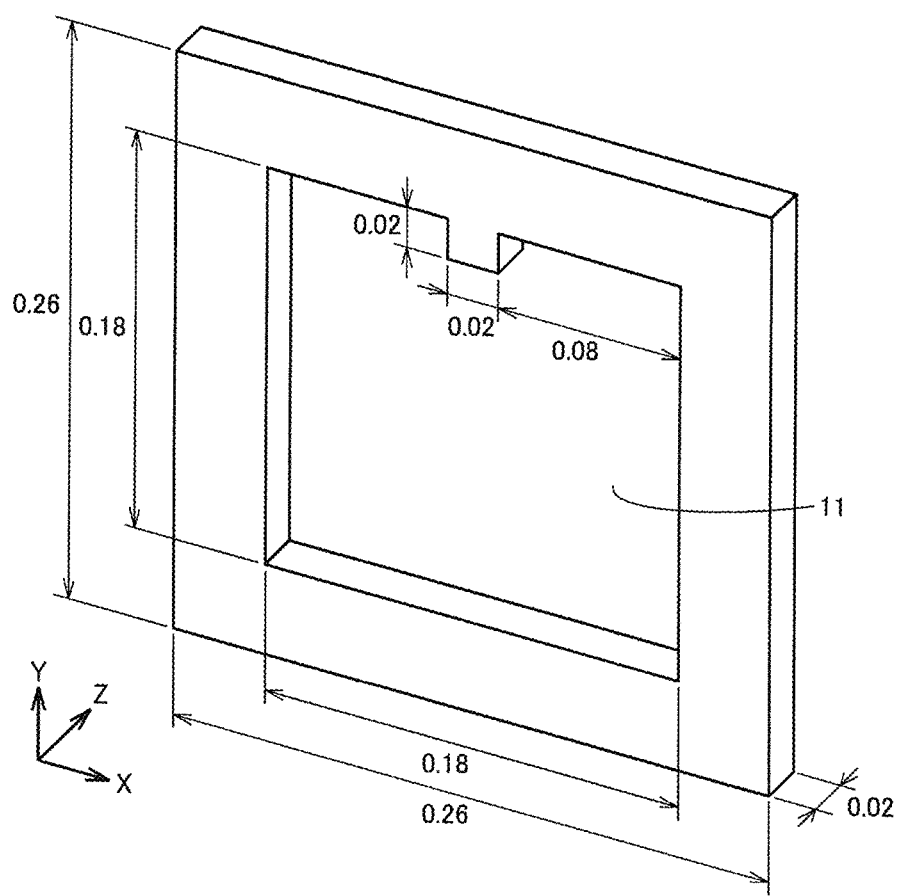
FIG. 1 is a perspective view of a unit structure configuring an example of a conventional void-arranged structure.

As a conventional void-arranged structure, used was a structure in which unit structures, one of which is illustrated in a perspective view in FIG. 1, were periodically arranged in an X-axis direction and a Y-axis direction. The unit structure shown in FIG. 1 includes a single void section 11, and the shape of the void-section 11 is so designed as not to be mirror-symmetric with respect to the Y-axis direction (with respect to a plane parallel to an X-Z plane) in order to generate a dip waveform. A thickness of the conductor is 20 µm (in the Z-axis direction) and the material thereof is a perfect conductor.

Figure 2:
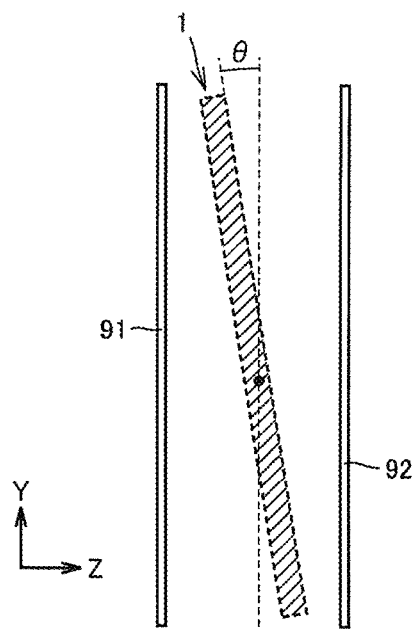
FIG. 2 is a schematic cross-sectional view for explaining an example of an installation state of a void-arranged structure.

A transmittance spectrum of the conventional void-arranged structure was obtained. Specifically, as shown in FIG. 2, the void-arranged structure 1 was disposed between two ports 91 and 92, and plane waves polarized in the Y-axis direction were emitted from the port 91 to be incident on a principal surface of the void-arranged structure 1 at right angles ($\theta=0$); then, a transmittance spectrum observed at the port 92 was obtained by the calculation using a FDTD method (finite-difference time-domain method). The distance between the void-arranged structure 1 and each of the ports 91 and 92 was set to be 600 μm. The obtained transmittance spectrum is shown in FIG. 3.

Figure 3:
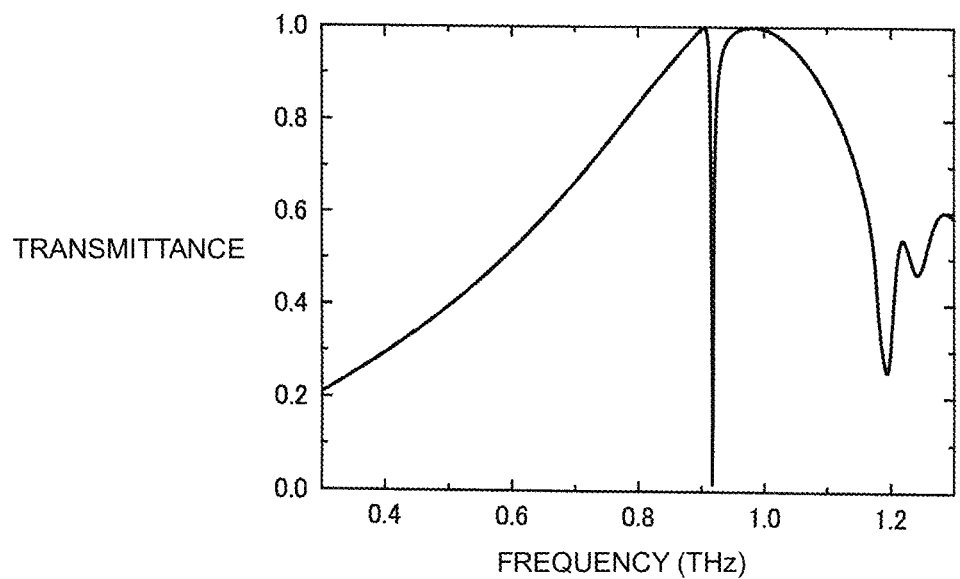
FIG. 3 is a diagram illustrating a transmittance spectrum of an example of a conventional void-arranged structure.

It is understood from FIG. 3 that a sharp dip waveform can be generated at a frequency of 0.917174 THz (917.174 GHz). It is well-known that the characteristics of the measurement object can be measured considering a change in shape of the dip waveform as shown in FIG. 3 (for example, see Patent Document 2).

Figure 4:
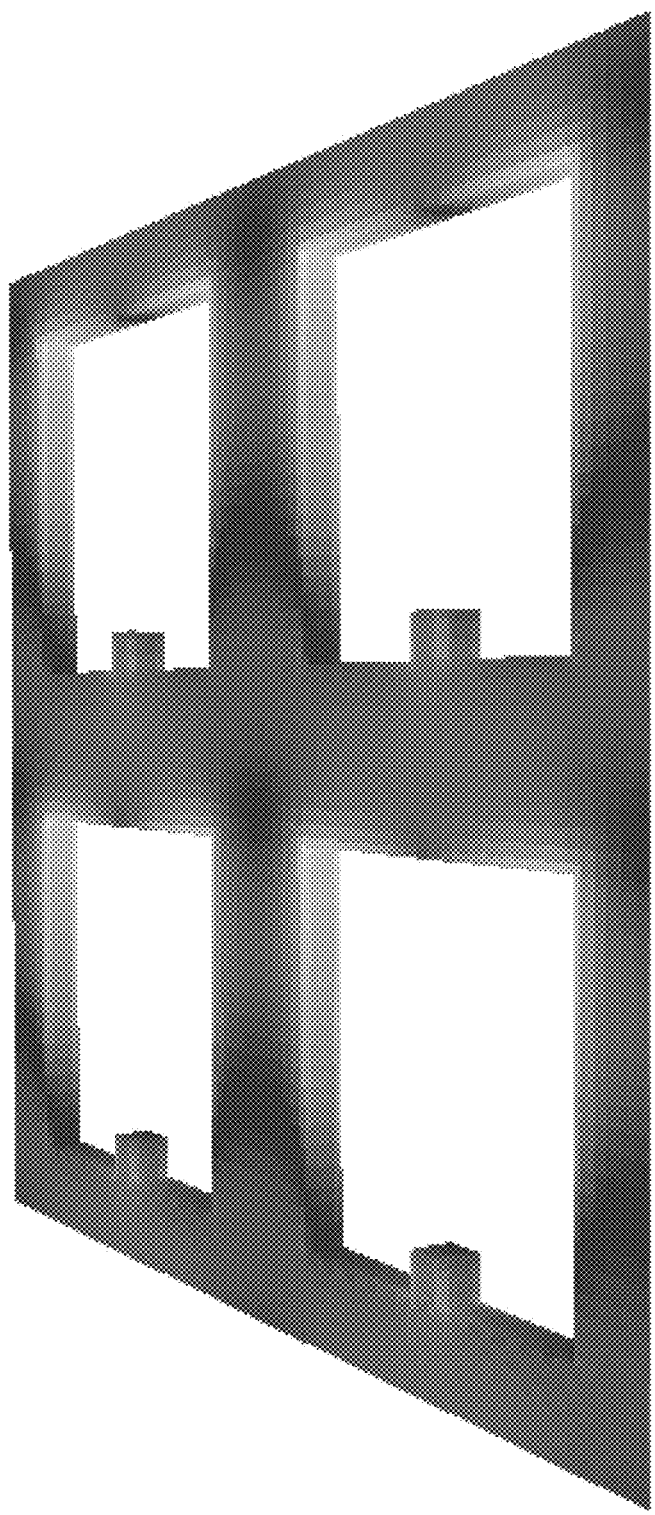
FIG. 4 is a diagram illustrating a current density distribution of an example of a conventional void-arranged structure.

FIG. 4 illustrates a current density distribution of the void-arranged structure at an arbitrary time with respect to the frequency (0.917174 THz) at which the dip waveform appears in FIG. 3. The void-arranged structure configured of the unit structures shown in FIG. 1 is designed so that the distribution of electric charges modulated at the frequency of 0.917174 THz is not mirror-symmetric with respect the Y-axis direction on a conductor portion located between the void sections adjacent to each other in the Y-axis direction. FIG. 4 illustrates the current density distribution at an arbitrary time; note that, however, the current density distribution is not mirror-symmetric with respect to the Y-axis direction at any time.

First Working Example

Figure 5:
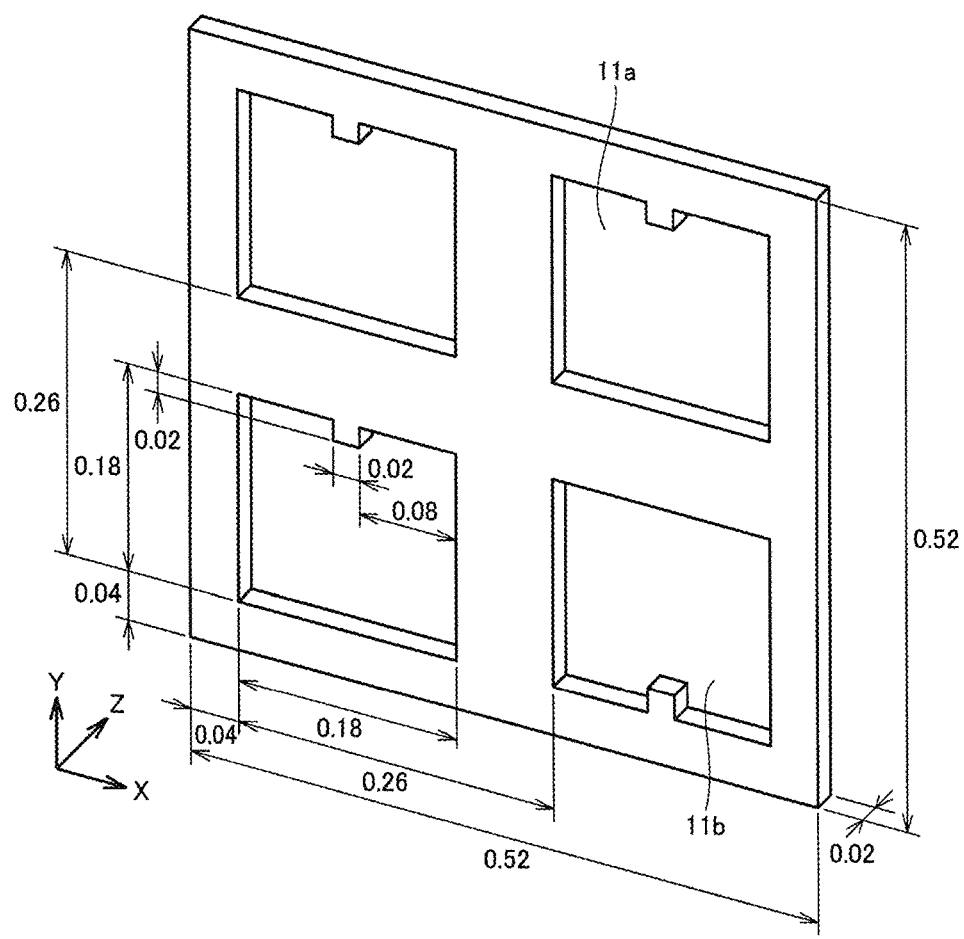
FIG. 5 is a perspective view of a unit structure configuring a void-arranged structure according to a first working example.

As a void-arranged structure of the first working example, used was a structure in which unit structures, one of which is illustrated in a perspective view in FIG. 5, were periodically arranged in the X-axis direction and the Y-axis direction. In the unit structure shown in FIG. 5, of the four void sections, only a second void section 11b on the lower right has a shape upside-down compared to the void section 11 shown in FIG. 1, and the other three first void sections 11a have the same shape as the shape shown in FIG. 1. In this manner, the unit structure shown in FIG. 5 is designed so that the overall shape thereof is not mirror-symmetric with respect to the Y-axis direction (a parallel plane with respect to the X-Z plane). A thickness of the conductor is 20 μm (in the Z direction) and the material thereof is a perfect conductor.

Figure 6:
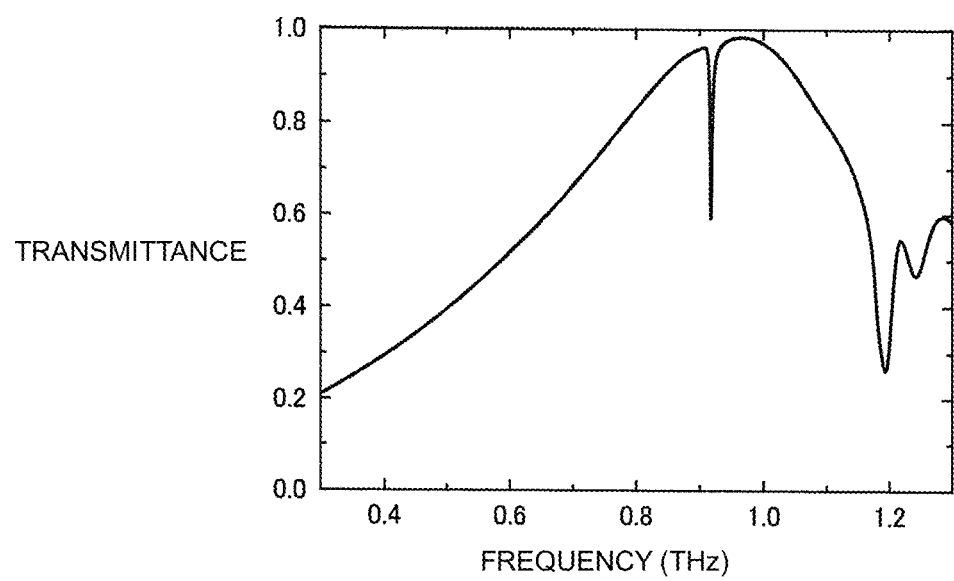
FIG. 6 is a diagram illustrating a transmittance spectrum of the void-arranged structure according to the first working example.

A transmittance spectrum of the void-arranged structure of the first working example was obtained in the same manner as in the conventional example. The obtained transmittance spectrum is shown in FIG. 6. It is understood from FIG. 6 that a sharp dip waveform can be generated at a frequency of 0.917694 THz (917.694 GHz).

Figure 7:
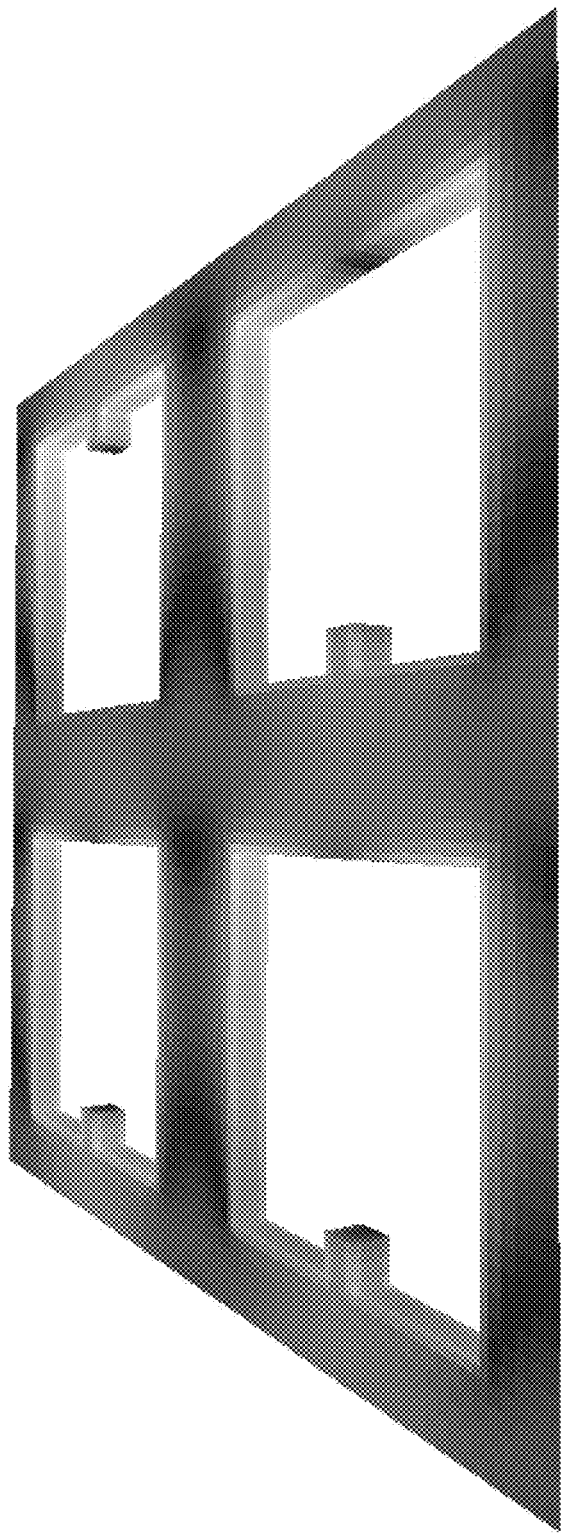
FIG. 7 is a diagram illustrating a current density distribution of the void-arranged structure according to the first working example.

FIG. 7 illustrates a current density distribution of the void-arranged structure at an arbitrary time with respect to the frequency (0.917694 THz) at which the dip waveform appears in FIG. 6. The unit structure shown in FIG. 5 is designed so that the distribution of electric charges modulated at the frequency of 0.917694 THz is not mirror-symmetric with respect the Y-axis direction on a conductor portion located between the void sections adjacent to each other in the Y-axis direction. FIG. 7 illustrates the current density distribution at an arbitrary time; note that, however, the current density distribution is not mirror-symmetric with respect to the Y-axis direction at any time.

When FIG. 7 is compared with FIG. 4, it is understood that the density of the current that flows on a surface of the void-arranged structure in FIG. 7 (particularly, the current density in the inner walls of the respective void sections (for example, a corner portion of the inner wall of each void section on the upper left viewed in a diagonal direction) is larger than that in the case of FIG. 4.

As discussed above, in the void-arranged structure of the present invention, at least one void section which does not have the same shape (facing the same direction) as the shape of the other void sections is included in a unit structure, whereby the current density distribution on the surface of the void-arranged structure largely changes when irradiated with electromagnetic waves (see FIGS. 4 and 7). This makes it possible to decrease a ratio of a portion on the surface of the void-arranged structure where the current density is small (thicker black portion in the drawing) and increase the current density particularly in the inner wall of the void section (thinner black portion in the drawing). Accordingly, in the case where the measurement object is attached to the void-arranged structure (in particular, in the case where it is attached to the inner wall of the void section), a change in characteristics of the scattered electromagnetic waves can be increased, whereby the measurement sensitivity can be improved.

First Comparative Example

Figure 8:
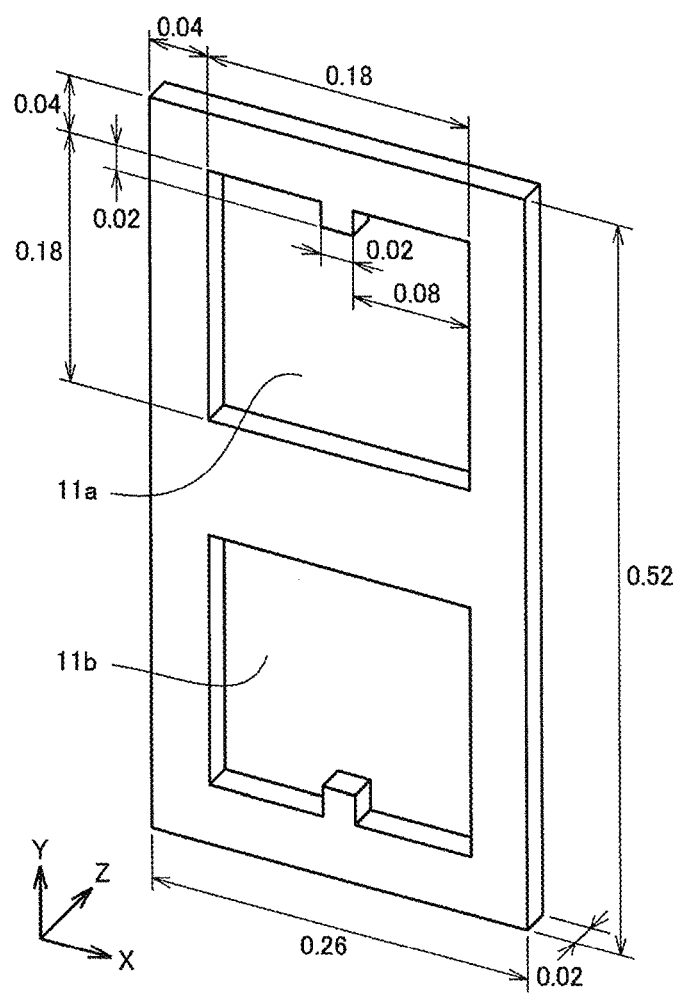
FIG. 8 is a perspective view of a unit structure configuring a void-arranged structure according to a first comparative example.

As a void-arranged structure of a first comparative example, used was a structure in which unit structures, one of which is illustrated in a perspective view in FIG. 8, were periodically arranged in the X-axis direction and the Y-axis direction. In the unit structure shown in FIG. 8, of the two void sections, the second void section 11b on the lower side has a shape upside-down compared to the void section 11 shown in FIG. 1, and the other first void section 11a has the same shape as the shape shown in FIG. 1. In this manner, the unit structure shown in FIG. 8 is so designed as to be mirror-symmetric with respect to the Y-axis direction (with respect to a plane parallel to the X-Z plane). A thickness of the conductor is 20 μm (in the Z direction) and the material thereof is a perfect conductor.

Figure 9:
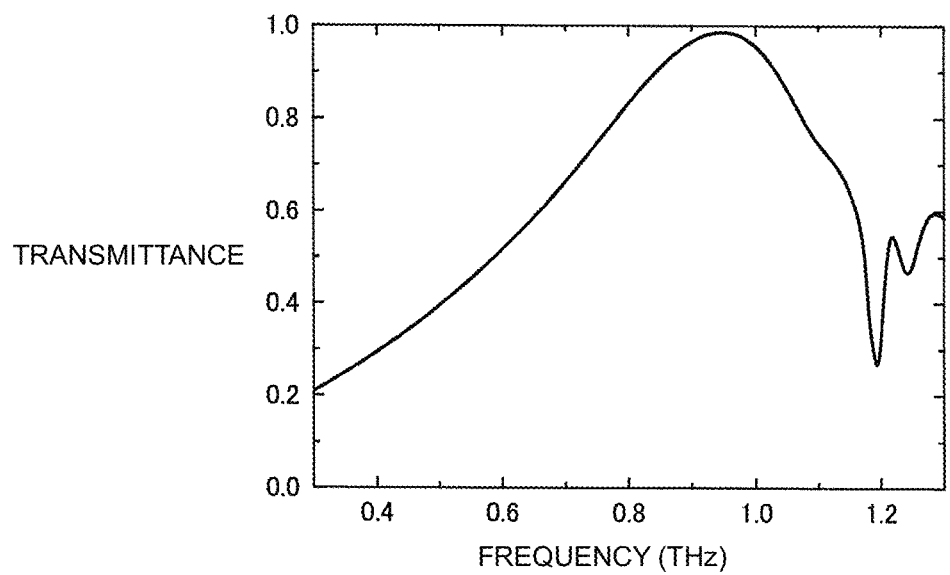
FIG. 9 is a diagram illustrating a transmittance spectrum of the void-arranged structure according to the first comparative example.

A transmittance spectrum of the void-arranged structure of the first comparative example was obtained in the same manner as in the conventional example. The obtained transmittance spectrum is shown in FIG. 9. It can be understood from FIG. 9 that a dip waveform is not generated in the first comparative example.

Second Comparative Example

Figure 10:
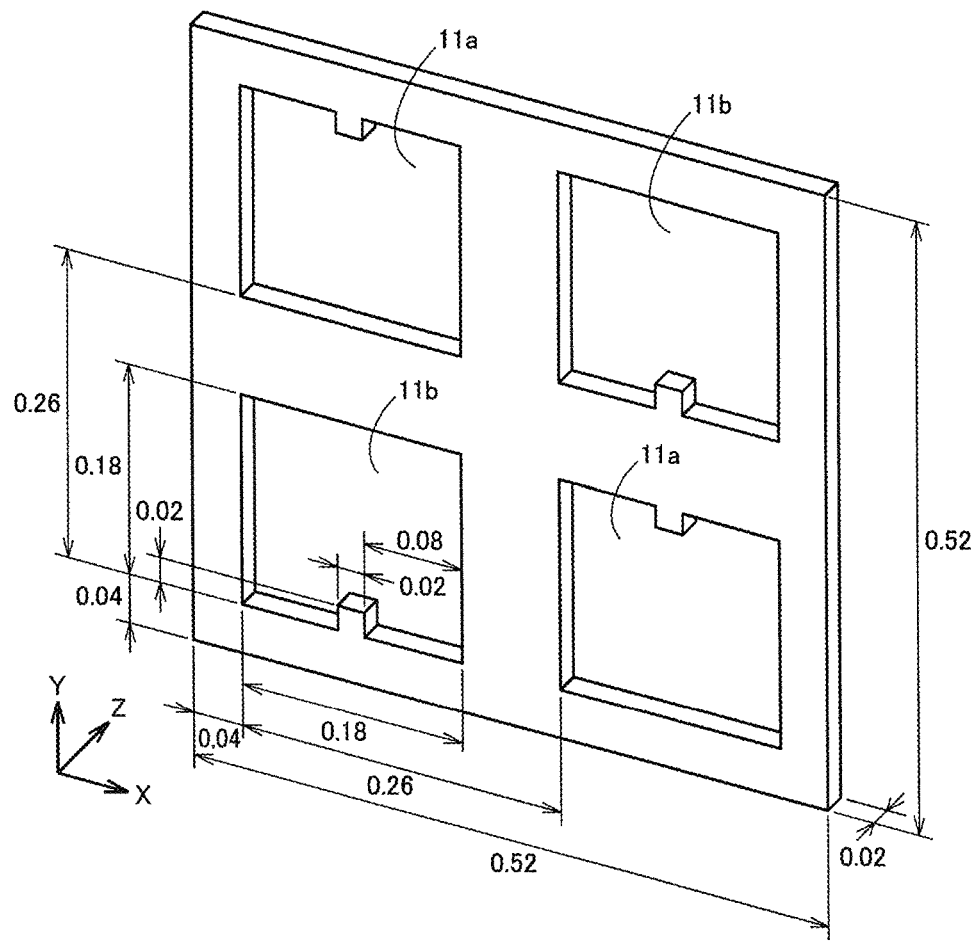
FIG. 10 is a perspective view of a unit structure configuring a void-arranged structure according to a second comparative example.

As a void-arranged structure of a second comparative example, used was a structure in which unit structures, one of which is illustrated in a perspective view in FIG. 10, were periodically arranged in the X-axis direction and the Y-axis direction. In the unit structure shown in FIG. 10, of the four void sections, two second void sections 11b on the lower left and upper right have a shape upside-down compared to the void section 11 shown in FIG. 1, and the other two first void sections 11a have the same shape as the shape shown in FIG. 1. In this manner, the unit structure shown in FIG. 10 is so designed as to be mirror-symmetric with respect to the Y-axis direction (with respect to a plane parallel to the X-Z plane). A thickness of the conductor is 20 μm (in the Z direction) and the material thereof is a perfect conductor.

Figure 11:
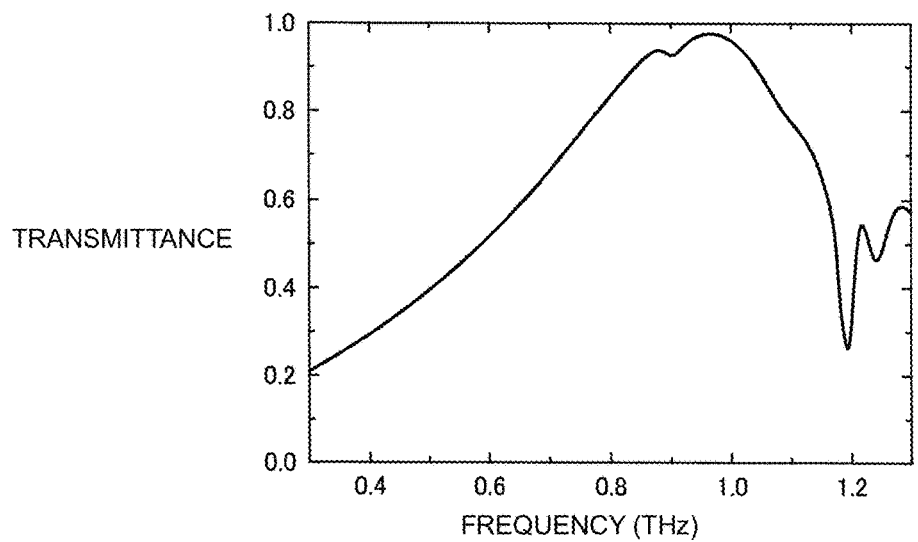
FIG. 11 is a diagram illustrating a transmittance spectrum of the void-arranged structure according to the second comparative example.

A transmittance spectrum of the void-arranged structure of the second comparative example was obtained in the same manner as in the conventional example. The obtained transmittance spectrum is shown in FIG. 11. It is understood from FIG. 11 that a dip waveform is slightly generated at the vicinity of 0.9 THz in the second comparative example. Based on this, the following can be considered: that is, even in the case where a unit structure includes a first void section and a second void section having a different shape from that of the first void section, a dip waveform is unlikely to be generated in the transmittance spectrum if the overall shape of the unit structure is mirror-symmetric with respect to a predetermined imaginary plane orthogonal to a principal surface of the void-arranged structure.

Second Working Example

Figure 12:
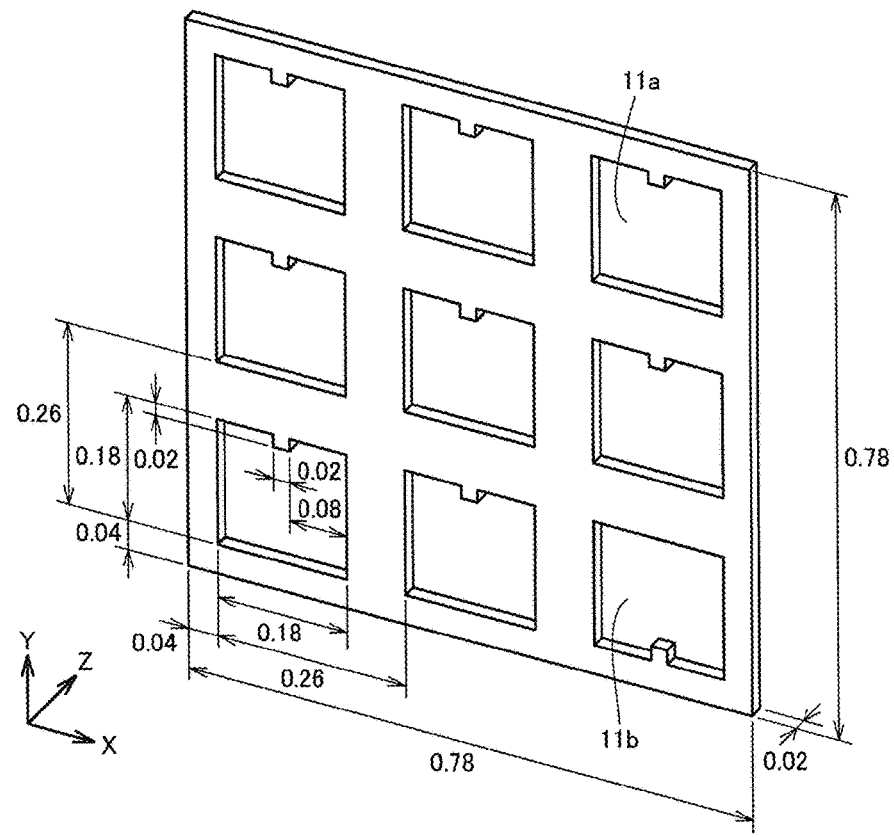
FIG. 12 is a perspective view of a unit structure configuring a void-arranged structure according to a second working example.

As a void-arranged structure of a second working example, used was a structure in which unit structures, one of which is illustrated in a perspective view in FIG. 12, were periodically arranged in the X-axis direction and the Y-axis direction. In the unit structure shown in FIG. 12, of the nine void sections, only the second void section 11b on the lower right has a shape upside-down compared to the void section 11 shown in FIG. 1, and the other eight first void sections 11a have the same shape as the shape shown in FIG. 1. In this manner, the unit structure shown in FIG. 12 is so designed as not to be mirror-symmetric with respect to the Y-axis direction (with respect to a plane parallel to the X-Z plane) in order to generate a dip waveform. A thickness of the conductor is 20 μm (in the Z direction) and the material thereof is a perfect conductor.

Figure 13:
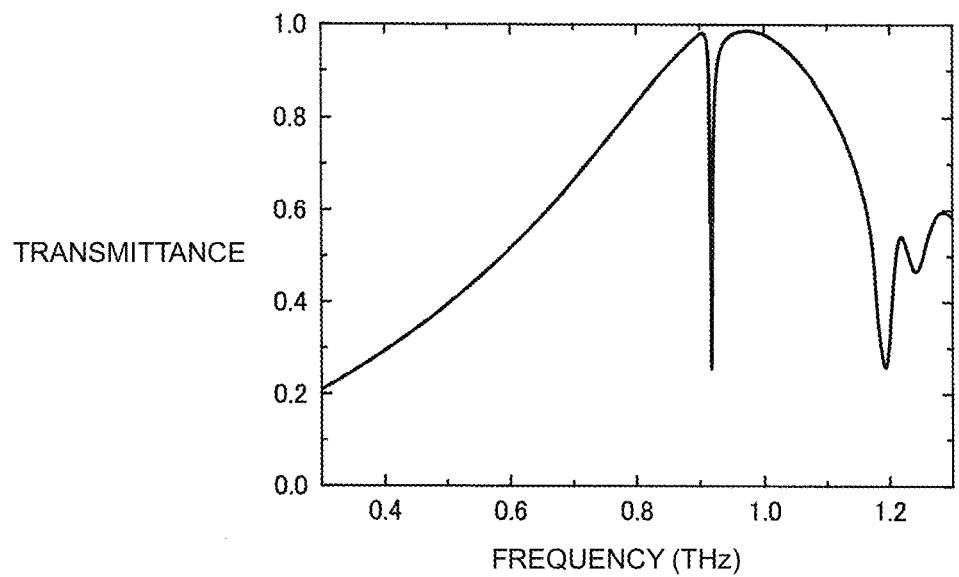
FIG. 13 is a diagram illustrating a transmittance spectrum of the void-arranged structure according to the second working example.

A transmittance spectrum of the void-arranged structure of the second working example was obtained in the same manner as in the conventional example. The obtained transmittance spectrum is shown in FIG. 13. It is understood from FIG. 13 that a sharp dip waveform can be generated at a frequency of 0.917362 THz (917.362 GHz).

The results discussed thus far exhibit that a dip waveform in a transmittance spectrum becomes sharper in the order of FIG. 11 (second comparative example), FIG. 6 (first working example), FIG. 13 (second working example), and FIG. 3 (conventional example). As such, it is understood that the dip wave form becomes sharper in the order of a case in which a ratio of the void sections having the same shape (the first void sections) to the total of the void sections included in a unit structure is 2/4, a case of the ratio being 3/4, a case of the ratio being 8/9, and a case of the ratio being 1/1.

Meanwhile, comparing FIG. 4 (conventional example) with FIG. 7 (first working example), the following can be understood: that is, in the case where a ratio of the void sections having the same shape (the first void sections) to the total of the void sections included in a unit structure is decreased to some extent, a ratio of a portion where a current density is small (thicker black portion in the drawing) decreases and a current density particularly in the inner wall of the void section tends to increase.

Accordingly, by appropriately decreasing a ratio of the first void sections to the total of the void sections within a unit structure from 100%, a change in characteristics of the scattered electromagnetic waves when a measurement object being attached to a surface of the void-arranged structure is increased and a dip waveform generated in a transmission spectrum becomes sharp, thereby making it possible to improve the overall measurement sensitivity. In other words, because the unit structure includes the first void section and the second void section having a different shape from that of the first void section and the overall shape of the unit structure is not mirror-symmetric with respect to a predetermined imaginary plane orthogonal to the principal surface of the void-arranged structure, the measurement sensitivity can be improved.

It should be noted that the embodiments and working examples disclosed herein are merely examples in all respects and are not limiting. The scope of the present invention is not defined by the descriptions given above, but by the scope of the appended claims, and it is intended to include any meanings equivalent to the scope of the claims and all modifications within the scope of the claims in the present invention.

REFERENCE SIGNS LIST

1 VOID-ARRANGED STRUCTURE
10a PRINCIPAL SURFACE
11 VOID SECTION
11a FIRST VOID SECTION
11b SECOND VOID SECTION
2 LASER
20 HALF MIRROR
21 MIRROR
22, 23, 24, 25 PARABOLIC SURFACE MIRROR
26 TIME DELAY STAGE
3 POWER SUPPLY
4 LOCK-IN AMPLIFIER
5 PC (PERSONAL COMPUTER)
6 AMPLIFIER
71, 72 PHOTOCONDUCTIVE ELEMENT
8 OSCILLATOR
91, 92 PORT

The invention claimed is:

1. A void-arranged structure comprising:
a pair of principal surfaces opposing each other; and
a plurality of unit structures, each unit structure of the plurality of unit structures including at least four void sections, the four void sections being aligned at a predetermined interval and connected two-dimensionally and periodically along a first direction and a second direction orthogonal to the first direction of a first principal surface of the pair of principal surfaces, and wherein each of the four void sections penetrate through the pair of principal surfaces, wherein
each of the at least four void sections includes three void sections having a same shape and one void section having a shape different from that of the three void sections, and
an overall shape of each unit structure, when viewed from the first principal surface, is not mirror-symmetric with respect to a predetermined imaginary plane orthogonal to the first principal surface of the void-arranged structure.

2. The void-arranged structure according to claim 1, wherein the imaginary plane is a plane perpendicular to a polarizing direction of electromagnetic waves irradiated on the void-arranged structure.

3. A measurement method for measuring a measurement object comprising:
holding a measurement object on the void-arranged structure according to claim 1;
irradiating the void-arranged structure on which the measurement object is held with electromagnetic waves and detecting characteristics of the electromagnetic waves having been scattered at the void-arranged structure; and
calculating a presence/absence or quantity of the measurement object from the detected characteristics of the electromagnetic waves.

4. The measurement method according to claim 3, wherein the electromagnetic waves strike the void-arranged structure in a direction perpendicular to at least one of the pair of principal surfaces of the void-arranged structure.

5. The measurement method according to claim 3, wherein the imaginary plane is a plane perpendicular to a polarizing direction of electromagnetic waves irradiated on the void-arranged structure.

* * * * *